United States Patent
Fogel

(12)
(10) Patent No.: US 6,548,557 B1
(45) Date of Patent: *Apr. 15, 2003

(54) NEUTRALIZATION OF PHOSPHATE ESTERS, COMPOSITIONS BASED UPON AND METHODS USING SAME

(75) Inventor: Arnold W. Fogel, Upper Saddle River, NJ (US)

(73) Assignee: Walter Merton Co., Inc., Englewood, NJ (US)

( * ) Notice: Subject to any disclaimer, the term of this patent is extended or adjusted under 35 U.S.C. 154(b) by 20 days.

This patent is subject to a terminal disclaimer.

(21) Appl. No.: 09/706,982

(22) Filed: Nov. 6, 2000

Related U.S. Application Data

(63) Continuation-in-part of application No. 09/511,736, filed on Feb. 6, 2000, now Pat. No. 6,417,238.

(51) Int. Cl.$^7$ .............................. B01F 17/14; B01F 3/08; A61K 7/00
(52) U.S. Cl. ..................... 516/24; 516/56; 516/907; 516/908; 424/401; 424/60; 514/939
(58) Field of Search .................. 516/24, 56, 907, 516/908; 558/72, 208, 213, 150; 424/401, 60; 514/939

(56) References Cited

U.S. PATENT DOCUMENTS

| | | | | |
|---|---|---|---|---|
| 3,180,786 A | * | 4/1965 | Domba et al. ............... | 516/125 |
| 3,972,914 A | | 8/1976 | Vanlerberghe et al. ...... | 560/263 |
| 4,016,341 A | * | 4/1977 | Ogawa et al. ............... | 427/230 |
| 4,118,443 A | * | 10/1978 | Klose ........................ | 549/218 |
| 4,612,384 A | | 9/1986 | Omura et al. ............... | 558/198 |
| 5,024,776 A | * | 6/1991 | Kreischer ................... | 510/221 |
| 5,141,741 A | * | 8/1992 | Ishida et al. ................. | 424/60 |
| 5,453,459 A | | 9/1995 | Roberts ....................... | 524/123 |
| 5,840,309 A | | 11/1998 | Herstein et al. ............. | 424/728 |
| 5,874,576 A | | 2/1999 | Huber ......................... | 544/211 |
| 5,993,861 A | * | 11/1999 | Fogel .......................... | 516/919 |
| 6,039,935 A | | 3/2000 | Mohammadi ................ | 424/59 |
| 6,417,238 B1 | * | 7/2002 | Fogel .......................... | 516/24 |

OTHER PUBLICATIONS

Hawley's Condensed Chemical Dictionary, Eleventh Edition (Van Nostrand Reinhold Company, NY, NY, copyright 1987) p. 1054, Oct. 1989.*

* cited by examiner

Primary Examiner—Daniel S. Metzmaier
(74) Attorney, Agent, or Firm—Henry D. Coleman; Coleman Sudol Sapone, P.C.

(57) ABSTRACT

The present invention relates to synthetic, novel, preferably fatty phosphoric acid esters which, when neutralized with a neutralizing agent, is revealed as a new surface active agent. Formulations are presented which demonstrate a method for using the disclosed surface active agent to prepare stable oil-in-water, water-in-oil emulsions and various solutions of varying polarity and viscosity for use in a variety of dermatological applications, and/or wherever emulsions or solutions according to the present invention may be used.

15 Claims, No Drawings

NEUTRALIZATION OF PHOSPHATE ESTERS, COMPOSITIONS BASED UPON AND METHODS USING SAME

RELATED APPLICATIONS

This application is a continuation-in-part application of Ser. No. 09/511,736, filed Feb. 6, 2000, issued as U.S. Pat. No. 6,417,238 on Jul. 9, 2002.

FIELD OF THE INVENTION

The present invention relates to borax neutralized phosphate esters (mono and/or diesters, predominantly monoesters) which, when preferably at least partially neutralized separately, or in situ, are revealed as novel emulsifiers. Formulations are presented also which demonstrate a method for using the disclosed emulsifier to prepare stable emulsions of varying polarity and viscosity for use in a variety of dermatological applications, and/or wherever this type of emulsion may be useful.

BACKGROUND OF THE INVENTION

From 1982 to 1995 the inventor marketed and sold diethanolamine (DEA) cetyl phosphate under the commercial name Amphisol™, as a technical sales representative for the Givaudan Corp. (Division of Hoffmann-LaRoche). A group of formulations including sunscreens, skin treatment and pigmented lotions, among others were formulated and demonstrated to help sell the Amphisol™ to sunscreen and skin care companies.

In the early 1990's, in Europe and in the United States in 1999, DEA derivatives became suspect and then undesirable for use because of possible nitrosamine formation and health concerns which emerged from this information.

In or about 1992–93, Amphisol™ K (the potassium salt of cetyl phosphate) was introduced to replace the Amphisol™ and thus eliminate the DEA. Amphisol™ K however, never functioned as well as the original Amphisol™ in certain applications. To this day, there is a desire by all users of Amphisol™ (who favor its inherent properties in making unusually stable oil-in-water emulsions) for a direct replacement which does not incorporate diethanolamine.

As early as 1957 the inventor was aware of the use of a beeswax-borax system to prepare water-in-oil emulsions. Although the system functions reasonably well, problems emerged as beeswax varied from batch to batch and produced quality control problems. In addition, compositions utilizing beeswax often required strenuous mixing or homogenization to facilitate the production of a stable final formulation.

In order to address the shortcomings of beeswax/borax, the present inventor invented emulsions based upon the neutralization product of 12-hydroxystearic acid. These formulations are described in U.S. Pat. No. 5,993,861, issued Nov. 30, 1999.

These diverse teachings and the inventor's experience after almost 40 years of research, led to the inventor's attempt to find an adequate replacement for the diethanolamine used in (DEA) cetyl phosphate, inasmuch as the art had failed to find an adequate replacement.

OBJECTS OF THE INVENTION

It is an object of the invention to provide phosphate ester surface active agents which function as one or more of emulsifiers, wetters, spreaders, dispersers, detergents, foamers and emollients to provide storage stable emulsions, among other compositions.

It is a further object of the invention to provide phosphate ester emulsifiers which can function as a direct replacement for diethanolamine (DEA) cetyl phosphate (Amphisol™).

It is an additional object of the invention to provide a method of making emulsions which are easy to formulate and provide for accurate quality control.

It is yet another object of the invention to provide emulsions which can be used to readily manufacture personal care products including cosmetic products such as sunscreens, skin care lotions and creams as well as a myriad of other types of products.

These and/or other objects of the invention may be readily gleaned from the detailed description of the invention which follows.

BRIEF DESCRIPTION OF THE PRESENT INVENTION

The present invention relates to phosphate ester surface active agents of the structure:

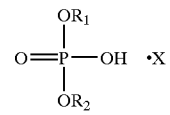

Where $R_1$ and $R_2$ are H or a linear, cyclic or branch chained saturated or unsaturated $C_8$–$C_{40}$ hydrocarbon group, more preferably a $C_{12}$–$C_{22}$ hydrocarbon group, a —$(R^3$—$O)_m$—$R^4$ group, a —$R^5$—$O$—$(R^3$—$O)_m$—$R^4$ group or a

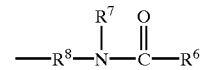

group, where $R^3$ is a $C_2$–$C_6$ alkylene group, preferably an ethylene group, a propylene group or a mixture of ethylene and propylene groups, $R^4$ is H or a linear, cyclic or branch chained saturated or unsaturated $C_8$–$C_{40}$ group, a

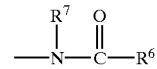

group or a

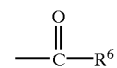

group,
$R^5$ is a $C_2$–$C_{18}$ alkylene group, $R^6$ is a linear, cyclic or branch chained saturated or unsaturated $C_8$–$C_{40}$ hydrocarbon group and m is an integer from 0 to 150, preferably 1 to 20, $R^7$ is H or a linear, cyclic or branch-chained saturated or unsaturated $C_1$–$C_{22}$ hydrocarbon group or a $C_1$–$C_{22}$ alcohol group and $R^8$ is a $C_1$–$C_{22}$ linear, cylic or branched chain saturated or unsaturated hydrocarbon group, with the proviso that when $R_1$ is H, $R_2$ cannot also be H and X is selected from the group consisting of $NaHCO_3$, $KaHCO_3$, $Na_2CO_3$, $K_2CO_3$, $Na_2HPO_4$, $K_2HPO_4$ $Na_2B_4O_7$.

Most preferably, $R_1$ is a $C_{16}H_{34}$ or cetyl group (such that the surface active agent is the cetyl ester of phosphoric acid neutralized with a neutralizing agent, preferably as an alkaline salt having a pH in water at 5% w/w of about 8–13), $R_2$ is H and X is $Na_2B_4O_7$. Thus, in preferred aspects according to the present invention, the neutralized surface active agent is an adduct (as distinguishable from a salt) prepared by the neutralization of a phosphoric acid ester containing one (neither $R_1$ nor $R_2$ is H) or two hydroxyl groups ($R_1$ or $R_2$ is H).

Surface active agents according to the present invention may be prepared by neutralizing a phosphoric acid ester in the presence of a neutralization compound preferably selected from the group consisting of $Na_2CO_3$, $K_2CO_3$, $NaHCO_3$, $KHCO_3$, $Na_2HPO_4$, $K_2HPO_4$, sodium tetraborate decahydrate (Borax NF), sodium tetraborate tetrahydrate and mixtures (for purposes of definition, the sodium tetraborate salts are considered "active boron salts" in the present invention), thereof. The surface active agents according to the present invention may be prepared in situ or separately, as isolated compounds. In situ means the phosphate ester is in the oil phase of the emulsion and the neutralizing salt is in the water phase. Then, the adduct is formed when the phases are mixed, thus forming the emulsifier in situ.

The surface active agents according to the present invention may be utilized to produce emulsions (primarily oil-in-water, but also water-in-oil as an auxiliary emulsifier in certain aspects) and for use in personal care products, such as creams and lotions, including pigmented formulations. The present compounds find particular use in emulsions, such as pigmented emulsions or moisturizing emulsions, among numerous others. The surface active agents according to the present invention which are emulsifiers exhibit excellent emulsification characteristics and, quite unexpectedly, also excellent emolliency. Surface active agents according to the present invention also may be used as wetters, spreaders, detergents, dispersers, solubilizers, and foamers as well as the previously mentioned emulsifiers and emollients. In addition, the surface active agents according to the present invention exhibit unusual solubility characteristics and can be dissolved in both hot water (70–75° C.) and hot oil (80–85° C.) at elevated temperatures. In addition, emulsifiers according to the present invention, when used in oil-in-water emulsions, form a water resistant film upon being deposited onto the skin- a characteristic which is excellent for sunscreens and other skin products. Emulsions according to the present invention exhibit consistent manufacturing and favorable storage stability even at high temperatures (50° C.).

Oil-in-water compositions according to the present invention comprise an oil phase and a water phase, with the oil phase generally ranging from about 5% to about 70% by weight of the emulsion composition and the water phase ranging from about 20% to about 90% by weight of the emulsion composition, the composition optionally containing additional components consistent with its use as an emulsion in a personal care product. More preferably, the oil phase in the composition ranges from about 10% to about 60% by weight of said composition, even more preferably about 10% to about 50% by weight of said composition. The water phase (such phase which, in in situ applications, generally includes the neutralization compound which reacts with the the phosphoric acid ester in the water phase and/or the oil phase to produce the emulsifier compound upon mixing the water and oil phases) comprises about 20% to about 90% by weight, preferably about 20% to about 75% by weight, more preferably about 25 to about 60% by weight of the emulsion composition.

In the present oil-in-water emulsion aspect of the present invention, the oil phase comprises an oil in a major amount (i.e., greater than about 50% by weight, more preferably at least about 70% and even more preferably about 75 to about 99.75% by weight of the oil phase) and as a minor component an emollient compound according to the chemical structure:

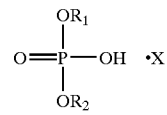

Where $R_1$ and $R_2$ are H or a linear, cyclic or branch chained saturated or unsaturated $C_8$–$C_{40}$ hydrocarbon group, more preferably a $C_{12}$–$C_{22}$ hydrocarbon group, a —$R^5$—O)$_m$—$R^4$ group, a —$R^5$—O—($R^3$—O)$_m$—$R^4$ group or a

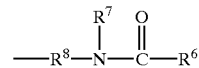

group,
where $R^3$ is a $C_2$–$C_6$ alkylene group, preferably an ethylene group, a propylene group or a mixture of ethylene and propylene groups, $R^4$ is H or a linear, cyclic or branch chained saturated or unsaturated $C_8$–$C_{40}$ group, a

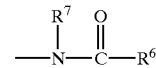

group or a

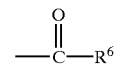

group,
$R^5$ is a $C_2$–$C_{18}$ alkylene group, $R^6$ is a linear, cyclic or branch chained saturated or unsaturated $C_8$–$C_{40}$ hydrocarbon group and m is an integer from 0 to 150, preferably 1 to 20, $R^7$ is H or a linear, cyclic or branch-chained saturated or unsaturated $C_1$–$C_{22}$ hydrocarbon group or a $C_2$–$C_{22}$ alcohol group and $R^8$ is a $C_1$–$C_{22}$ linear, cylic or branched chain saturated or unsaturated hydrocarbon group, with the proviso that when $R_1$ is H, $R_2$ cannot also be H and X is selected from the group consisting of $NaHCO_3$, $KaHCO_3$, $Na_2CO_3$, $K_2CO_3$, $Na_2HPO_4$, $K_2HPO_4$ and $Na_2B_4O_7$.

Most preferably, $R_1$ is a $C_{16}H_{34}$ or cetyl group (such that the surface active agent is the cetyl ester of phosphoric acid neutralized with a neutralizing agent, preferably as an alkaline salt having a pH in water at 5% w/w of about 8–12), $R_2$ is H and X is $Na_2B_4O_7$. Thus, in preferred aspects according to the present invention, the neutralized surface active agent is an adduct prepared by the neutralization of a phosphoric acid ester containing one (neither $R_1$ nor $R_2$ is H) or two hydroxyl groups ($R_1$ or $R_2$ is H).

In the aspect of the present invention which relates emulsions, the emollient compound is used in amounts comprising about 0.25% to about 30% by weight of the final emulsion composition (which contains both oil phase and water phase), more preferably, about 0.5% to about 20% by weight of the final emulsions composition, even more preferably about 1.0% to about 10% by weight of the final emulsion composition. In the oil-in-water emulsions according to the present invention, the amount of oil in the oil phase preferably ranges from about 70% to about 99.75% by weight, more preferably, about 80% to about 99.5% by weight, even more preferably about 92.5% to about 99% by weight. It is noted here that the amount of the surface active agent and and oil to be included within the oil phase will vary depending upon the amount of water to be included in the final emulsion composition, noting that in oil-in-water emulsions the amount of surface active agent included will tend to be considerably greater than in the case of a water-in-oil emulsion composition. Also, as a general rule, regardless of whether one is dealing with an oil-in-water emulsion or a water-in-oil emulsion, as the amount of water increases in the emulsion composition, the amount of the surface active agent which is included in the emulsion composition also generally increases, whereas the amount of oil tends to decrease.

In certain in situ aspects according to the present invention, the water phase may also include an amount of a "neutralizing agent or compound" effective to produce an emulsion when the water phase and oil phases are combined. Examples of such neutralizing compounds include, for example, boron-containing compounds such as sodium tetraborate decahydrate (Borax NF), and sodium tetraborate tetrahydrate, disodium monohydrogen phosphate and dipotassium monohydrogen phosphate, sodium carbonate, potassium carbonate, sodium bicarbonate, potassium bicarbonate and mixtures thereof.

Emulsion compositions according to the present invention may also include optional additives, for example, fragrances, preservatives, anti-oxidants, vitamins, pigments, conditioning agents, among numerous other standard cosmetic additives. These additives may be included in emulsion compositions according to the present invention in amounts up to about 25% by weight, preferably, in amounts ranging from about 0.01% to about 10% by weight, most preferably less than about 5% by weight within this range. The inclusion of these components does not change the basic and novel characteristics of the present compositions which relates to the use of the emulsion compositions according to the present invention being useful as or in personal care products.

DETAILED DESCRIPTION OF THE INVENTION

The term "surface active agent" is used throughout the specification to describe neutralized phosphoric acid esters (adducts) according to the general structure which is set forth above. Surface active agents according to the present invention may be used as one or more of emulsifiers, wetters, spreaders, dispersers, foamers and emollients in effective amounts in compositions according to the present invention. The term "effective" is used generally to describe amounts of compounds according to the present invention which are added to compositions to produce an intended effect.

Surface active agents according to the present invention exhibit advantageous features which are related to their chemical structure. For example, surface active agents according to the present invention are advantageous for their anionic character, thus making preservation with Germaben and related preservatives significantly easier than with non-ionic or cationic surface active agents. Surface active agents according to the present invention also exhibit unusual solubility and an ability to function at various pH's. These agents are soluble in hot oil and hot water, but not in cold water or oil, thus making the agents useful in making oil-in-water emulsions which act like water-in-oil emulsions. These agents are particularly useful for formulating waterproof sunscreens and handcreams without requiring the inclusion of a waterproofing polymer. In addition, surface active agents according to the present invention provide unusually stable emulsions even at temperatures as high as 50° C. (or even higher) and can be used effectively in amounts as low as about 1% to about 3% (or even lower) by weight of a final composition. These characteristics are unexpected attributes or characteristics of the present surface active agents.

The terms "emulsion", "oil-in-water emulsion" and "water-in-oil emulsion" are used throughout the specification to describe certain compositions according to the present invention which contain in its broadest aspect, a water phase, an oil phase and an emulsfier. An "emulsion" according to the present invention is a cream or lotion which is generally formed by the suspension of a very finely divided liquid, in this case water, in another liquid, in this case, an oil. In the present invention, an oil-in-water emulsion is formed when the oil phase is compatabilized in the water phase such as that the oil phase becomes hidden within the water phase. A water-in-oil emulsion is formed when the water phase is compatibilized in the oil phase, such that the water phase becomes "hidden" within the oil phase. While not being limited by way of theory, it is believed that in the emulsion compositions according to the present invention, the oil and/or the water phase produces an encapsulation-like structure or a related structure surrounding water (water-in-oil emulsion) or oil phase (oil-in-water emulsion), with the reaction product of the phosphoric acid ester and neutralizing compound serving to cause or enhance the formation of the emulsion composition. The term emulsion is used to distinguish the present compositions from compositions which contain at least two distinct phases, i.e., an oil phase and a water phase. Phosphoric acid ester surface active agents according to the present invention exhibit primary emulsifier activity in oil-in-water emulsions and are excellent secondary or auxiliary emulsifiers for use in water-in-oil emulsions.

The term "hydrocarbon" is used throughout the specification to describe R ($R_1$ and $R_2$) groups according to the present invention. R may be a linear or branch chained saturated or unsaturated $C_8$–$C_{40}$ hydrocarbon group, more preferably, a $C_{10}$–$C_{22}$ hydrocarbon group, even more preferably, a $C_{16}H_{34}$ group. The term hydrocarbon embraces, but is not limited to, for example, alkyl, alkene groups (including those groups containing more than one unsaturated double bond), alkyne groups, aryl groups, aralkyl groups and related groups which are comprised of carbon and hydrogen atoms. Groups which may be found on fatty amines according to the present invention also may be described as hydrocarbons, although the number of carbon atoms which are found in hydrocarbon groups in the fatty amine according to the present invention falls within a more narrow range than do the hydrocarbon groups which may be used as R groups in stearic acid esters or surface active agents according to the present invention.

The term "oil" or "emollient oil" is used throughout the specification to describe any of various lubricious, hydrophobic and combustible substances obtained from animal, vegetable and mineral matter which function as emollients on the skin. Oils for use in the present invention may include petroleum-based oil derivatives such as purified petrolatum and mineral oil. "Non-polar" oils are generally oils such as petrolatum or mineral oil or its derivatives which are hydrocarbons and are more hydrophobic and lipophilic compared to synthetic oils, such as esters, which may be referred to as "polar" oils. It is understood that within the class of oils, that the use of the terms "non-polar" and "polar" are relative within this very hydrophobic and lipophilic class, and all of the oils tend to be much more hydrophobic and lipophilic than the water phase which is used in the present invention.

In addition to the above-described oils, certain essential oils derived from plants such as volatile liquids derived from flowers, stems and leaves and other parts of the plant which may include terpenoids and other natural products including triglycerides may also be considered oils for purposes of the present invention.

Petrolatum (mineral fat, petroleum jelly or mineral jelly) and mineral oil products for use in the present invention may be obtained from a variety of suppliers. These products may range widely in viscosity and other physical and chemical characteristics such as molecular weight and purity. Preferred petrolatum and mineral oil for use in the present invention are those which exhibit significant utility in cosmetic and pharmacuetical products. Cosmetic grade oils are preferred oils for use in the present invention.

Additional oils for use in the present invention may include, for example, mono-, di- and tri- glycerides which may be natural or synthetic (derived from esterification of glycerol and at least one organic acid, saturated or unsaturated, such as for example, such as butyric, caproic, palmitic, stearic, oleic, linoleic or linolenic acids, among numerous others, preferably a fatty organic acid, comprising between 8 and 26 carbon atoms). Glyceride esters for use in the present invention include vegetable oils derived chiefly from seeds or nuts and include drying oils, for example, linseed, iticica and tung, among others; semi-drying oils, for example, soybean, sunflower, safflower and cottonseed oil; non-drying oils, for example castor and coconut oil; and other oils, such as those used in soap, for example palm oil. Hydrogenated vegetable oils also may be used in the present invention. Animal oils are also contemplated for use as glyceride esters and include, for example, fats such as tallow, lard and stearin and liquid fats, such as fish oils, fish-liver oils and other animal oils, including sperm oil, among numerous others. In addition, a number of other oils may be used, including $C_{12}$ to $C_{30}$ (or higher) fatty esters (other than the glyceride esters, which are described above) or any other acceptable cosmetic emollient.

Preferred oils for use in the present invention include petrolatum, mineral oil or mixtures of petrolatum and mineral oil where the amount of petrolatum to mineral oil (on a weight/weight basis) ranges from about 1:20 to about 10:1, preferably about 1:5 to about 5:1, depending upon the end use of the emulsion composition. The inclusion of petrolatum and/or mineral oil and/or the ratio of petrolatum to mineral oil in the present compositions will influence the final viscosity of the water-in-oil or oil-in-water compositions according to the present invention.

The term "storage stability" is used throughout the specification to describe a characteristic of emulsion compositions according to the present invention which relates to the fact that the present emulsions are generally storage stable at 50° C. for a period of at least about three months, and often longer than six months, a year or even longer. This is an advantageous feature of emulsion compositions according to the present invention and occurs, at least in part, because of the manufacturing consistency of the product.

The term "neutralizing agent" or "neutralizing compound" is used throughout the specification to describe a compound which is reactive with the phosphoric acid group of the phosphoric acid ester to produce an adduct phosphoric acid ester in an amount effective to produce a stable emulsion when a water phase, an oil phases and an effective amount of an surface active agent are combined. In the present invention, the neutralizing agent or compound reacts or complexes with the phosphoric acid moiety of the phosphoric acid ester compound to form an adduct. A neutralizing compound for use in the present invention may be any alkaline compound (generally a salt or other compound which produces a pH ranging from about 8–13 in a 5% aqueous solution) which forms a complex or adduct with the phosphoric acid ester compound. In certain embodiments according to the present invention, preferred neutralizing compounds include any alkaline salt whose 5% aqueous solution gives a pH ranging from about 8 to about 12, preferably about 9–11. Preferred alkaline salts include, for example, $Na_2HPO_4$, $K_2HPO_4$ $Na_3PO_4$, $K_3PO_4$, $NaHCO_3$, $KHCO_3$, $Na_2CO_3$, $K_2CO_3$, $Na_2B_4O_7 \cdot 4H_2O$, $Na_2B_4O_7 \cdot 10H_2O$, and mixtures thereof, among others. The most preferred alkaline salts for use in the present invention include the active boron salts, such as $Na_2B_4O_7 \cdot 4H_2O$, $Na_2B_4O_7 \cdot 10H_2O$, among others. In the present invention, the amount of neutralizing compound to phosphoric acid ester compound used in the final emulsion composition ranges from about 1 part (weight/weight) to 10 to about 2 parts to 1, more preferably about 1:4 to about 1:3, more preferably about 1:2. The amount of neutralizing compound to phosphoric acid ester compound used in the present compositions is not necessarily a stoichiometric amount. It is noted that this amount should serve as a guide, but not to limit, the understanding as to the amount of neutralizing compound to be used in the present invention. Examples of neutralizing compounds for use in the present invention include, for example, boron-containing compounds such as sodium tetraborate decahydrate (Borax NF), sodium tetraborate tetrahydrate, $Na_2HPO_4$ or $K_2HPO_4$, $Na_3PO_4$, $K_3PO_4$, $NaHCO_3$, $KHCO_3$, $Na_2CO_3$, $K_2CO_3$, and mixtures thereof. Preferred neutralizing compounds which are used in the present invention include the active boron salts, for example, sodium tetraborate decahydrate (Borax NF) and sodium tetraborate tetrahydrate, with sodium tetraborate decahydrate (Borax NF) being the most preferred neutralizing agent for use in the present invention.

The term "self-emulsifier" or "'self-emulsification" is used to describe compounds according to the present invention which are the reaction products of a phosphoric acid ester compound and a neutralizing compound according to the present invention and may be used to create emulsion compositions according to the present invention by simple mixing, i.e., without relying on shear forces or high speed mixing action. These surface active agents may be created in situ by mixing the phosphoric acid ester compound with the neutralizing compound during formation of the emulsion, or alternatively, may be prepared separately, by neutralizing the phosphoric acid ester with the neutralizing compound and then adding the pre-formed surface active agent to other components to form the emulsion composition.

The term "secondary emulsifier" or "helper emulsifer" is used throughout the specification to describe compounds which are added to the emulsifier compositions according to the present invention to provide a more stable and in some embodiments consistent emulsion composition, generally an oil-in-water emulsion composition. Secondary or helper emulsifiers may be advantageous when formulating oil-in-water emulsion compositions which utilize one or more salts such as the phosphate salts or carbonate salts to neutralize the phosphoric acid ester in producing the emulsifier compound. Secondary emulsifiers as used in an oil-in-water aspect of the present invention generally are considered surfactants which exhibit good surface activity and produce a low interfacial tension in the system in which it is used. Secondary emulsifiers preferably used in the present oil-in-water emulsions exhibit a tendency to migrate to the interface, rather than remain dissolved in either one of the water or emollient oil phase. Mixtures of secondary emulsifiers actually may be preferred in certain embodiments, where the need is to provide better interaction between the oil and water phases. Secondary emulsifiers have been advantageously used in the present invention where the neutralizing agent is or contains at least one phosphate or carbonate salt, or where the oil is a synthetic ester or more polar oil. One of ordinary skill in the art may readily determine the type of emulsifier or emulsifying system (group of emulsifiers) which may be used in the oil-in-water emulsions according to the present invention. A secondary emulsifier is used in the present invention in an amount effective to aid or promote emulsification of the water phase and oil phase ("emulsification effective amount"). As a general rule, the amount of secondary emulsifer which is included in compositions according to the present invention ranges from about 0.01% to about 10% by weight, more preferably about 0.1% to about 5.0% by weight of the final emulsion composition. In oil-in-water emulsion compositions according to the present invention, where secondary emulsifiers are optionally included, the weight ratio of phosphoric acid ester emulsifiers according to the present invention to secondary emulsifier ranges from about 20:1 to about 1:20, more preferably about 10:1 to about 1:1.

Exemplary secondary emulsifiers for use in oil-in-water emulsions according to the present invention may be any cosmetically acceptable oil soluble non-ionic or anionic (and in rare instances quaternary or amphoteric) surfactant which has a hydrophilic group ("tail") at one end of the molecule, of which polyethylene glycol 1500 dihydroxystearate (Arlacel P135®, available from ICI Americas, Inc) is particularly preferred, although a large number of other secondary emulsifiers may be used in the present invention. One of ordinary skill will understand to include one or more secondary emulsifiers in emulsion compositions according to the present invention in order to facilitate and enhance interaction of the water and oil phases.

In certain aspects of the present invention which relate to water-in-oil emulsions, the phosphoric acid ester surface active agent compounds according to the present invention are preferably used as secondary or auxiliary water-in-oil emulsifiers, in amounts which generally range from about 0.01% up to about 10% by weight, more preferably about 0.1% to about 5.0%by weight of the water-in-oil emulsion compositions.

In addition to phosphoric acid ester compounds, an oil, water and neutralizng compound, the emulsion compositions (whether oil-in-water or water-in-oil) may also comprise, in amounts totalling up to about 25% by weight of the final emulsion composition, preferably comprising about 0.001% to about 10% by weight, even more preferably no more than about 5% by weight within this range, one or more optional additive selected from among one or more secondary emulsifier, fragrances, preservatives, antioxidants, vitamins, pigments, conditioning agents, humectants and coloring agents among numerous other standard cosmetic additives.

Phosphoric acid ester compounds (i.e., the phosphoric acid ester reactant which forms a phosphoric acid ester surface active agent compound) according to the present invention are generally made by reacting phosphoric acid with an alcohol to produce a mono- or diester of phosphoric acid (generally the product will be a mixture of the mono and diester of phosphoric acid). More complex alcohols are generally prepared by forming or releasing the free alcohol group last (a blocking group, for example may be used during synthesis, which may be removed prior to reaction with phosphoric acid) and then reacting the free alcohol group with phosphoric acid as described above to produce the phosphoric acid ester or diester. Using the phosphoric acid ester or diester as described above, the phosphoric acid ester surface active agent is obtained by reacting the ester in water or a mixture of water and a solvent such as ethanol or isopropanol (among other solvents, depending upon the solubility of the ester and the final phosphoric acid ester surface active agent) in the presence of borax, N.F. or alternative neutralizing agent. In the reaction, the phosphoric acid ester before neutralization has a pH which falls within the range of less than 1 to about 1.0 (up to about 2.0), depending upon the concentration of phosphoric acid ester used. An excess of neutralizing agent may be added to the solution of phosphoric acid ester, the reactants are stirred and heated to a temperature of about 70° C. for a period sufficient to have the solution become neutral (a pH ranging from about 6.0 to about 8.0), at which time, the solution usually becomes clear. In preferred embodiments, upon cooling, generally to about room temperature, the phosphoric acid ester surface active agent compound will precipitate out of solution and the compound can be collected by simple filtration. In cases where the surface active agent is more soluble in the water/solvent mixture, the solvent may need to be evaporated off and the water cooled to crystallize the surface active agent compound out of solution. The surface active agent compound may be used without further purification or mayt be recrystallized to produce a compound of higher purity. The pH of the final compound may range from acidic to basic, but is preferably neutral (pH about 6.0 to about 8.0) unless the adduct requires the pH to fall outside this range (for example, a basic pH to promote stability of a carbonate or bicarbonate adduct).

Oil-in-water emulsion compositions according to the present invention may be made by mixing the individual components in any order at elevated temperature, but are preferably made by first preparing the oil phase and water phase at elevated temperature (preferably, above about 70–75° C., more preferably above about 85° C.) separately, then combining the oil phase with the water phase also at an elevated temperature (preferably, in the case of oil-in-water emulsions by adding the oil phase to the water phase) such that the oil phase remains soluble within itself during mixing. Generally, the temperature at which mixing is effected is preferably at least about 50° C., more preferably at least about 65 to 75° C., even more preferably at least about 75 to 85° C., and most preferably at least about 85° C. These are temperatures which are generally effective to allow the oil phase to remain soluble within itself (at a temperature wherein the oil phase remains clear and in a solution) during mixing. After mixing for at least about 10–15 minutes, more preferably at least 30 minutes or more (depending upon batch size) at elevated temperatures, the mixture is then cooled before use and/or packaging. Mixing may be performed in a simple propeller mixer with vortex formation without the application of high shear force, although in certain cases high shear force may be desirable. Although one could use higher mixing speeds, the emulsifiers according to the present invention, which tend to be self-emulsifiers, make mixing the compositions relatively easy.

All components may be mixed together in a one pot preparation, or one or more components (such as the oil phase, water phase or surface active agent) may be prepared separately and then combined. In preferred embodiments, after the separate water and oil phases are prepared, the oil phase is added to the water phase and the combined phases are mixed thoroughly for maximum result. It is noted that the preferred method for making the present composition comprises first making the water and oil phases separately, preferably adding the oil phase to the water phase, followed by mixing the phases together, all at elevated temperature. Alternatively, it is possible to separately mix the individual components in a single pot preparation or prepare the complex of the stearic acid ester compound and the neutralizing compound before it is added to the oil and/or water phases.

It is noted that the phosphoric acid ester surface active agent compounds of the present invention is more efficient at producing an oil-in-water emulsion than a water-in-oil emulsion. In addition, the use of non-polar oils may be more readily accommodated than polar oils in an oil-in-water emulsion using phosphoric acid ester emulsifier compounds of the present invention. In certain instances, when utilizing polar oils or emollients, either alone or in combination with a non-polar oil, at least one additional secondary or helper emulsifier may be advantageously added to produce a superior emulsion composition. In certain embodiments, therefore, the inclusion of a secondary emulsifer may be advantageously employed. Preferred secondary emulsifiers for inclusion in the present emulsion compositions include for example, polyethyleneglycol 1500 dihydroxystearate (Arlacel P135®™, available from ICI Americas, Inc.), in amounts generally ranging from about 0.01% to about 10% (up to about 20% by weight of the final emulsion composition), more preferably about 0.1% to about 5%, by weight of the final emulsion composition.

Emulsion compositions according to the present invention have inversion temperatures of at least about 40–45° C., preferably at least about 50° C., more preferably at least about 60° C. or higher. Inversion temperatures of at least about 65° C. may be particularly preferred. The higher the inversion temperature of an emulsion composition according to the present invention, generally, the more stable is the emulsion composition.

Having generally described the invention, reference is now made to the following examples which are intended to illustrate preferred embodiments and comparisons but which are not to be construed as limiting to the scope of this invention as is more broadly set forth above and in the appended claims.

EXAMPLES

Example I

Synthesis of Borax Neutralized Cetyl Phosphate

This is the preferred neutralized salt of the present invention and its method of making.

| Materials: | % Weight |
|---|---|
| Isopropanol, 99% | 35.0% |
| Water, Deionized | 35.0% |
| Cetyl Phosphate[1] | 20.0% |
| Borax, N.F. | 10.0% |
| Total | 100% |

Procedure: The materials are combined and heated all together at a temperature of about 70° C. until the solution becomes clear. The solution is then cooled to room temperature or slightly higher- about 25–30° C. and after the surface active agent crystallizes out of solution, it is filtered, dried and used.

1—Available as Amphisol A from Roche Chemical, Inc.

Example II

Suntan Cream SPF 30 Utilizing In Situ Generation of Emulsifier

| | Component | Weight % | Class of Compound |
|---|---|---|---|
| Phase A: (mix and dissolve at 85° C.) | Cetyl Phosphate Amphisol A (Roche) | 2.0 | Emulsifier |
| | Glyceryl Monostearate, Neutral (Cerasynt SD-ISP) | 4.0 | Thickener |
| | Cetyl Alcohol | 2.0 | Thickener |
| | Marrix ® 2,2,2 Dibehenyl Fumarate Bernel Chemical Co., Inc. | 2.0 | Thickener |
| | Elefac I-205 (Octyl dodecyl Neopentanoate) Bernel Chemical Co., Inc. | 10.0 | Emollient |
| | Octyl Methoxy Cinnamate | 7.5 | Sunscreen |
| | Octyl Salicylate | 5.0 | Sunscreen |
| | Oxybenzone | 5.0 | Sunscreen |
| | Dow Corning Silicone 200–350 cs | 0.5 | Anti-Foamer |
| | Ganex V-220 (PVP-eicosamine-ISP) | 3.0 | Waterproofing polymer |
| Phase B: (Dissolve At 85° C.) | Water, deionized | 56.5 | |
| | Borax N.F. | 1.5 | Neutralizing Agent |

| | Component | Weight % | Class of Compound |
|---|---|---|---|
| Phase C | Germaben II (ISP) | 1.0 | Preservative |
| | | 100.0% total | |

The procedure used was as follows:

Phase A and B are mixed well at a temperature of 80–85° C., Phase C is then added to the well mixed A and B mixture and the complete mixture is mixed further until thoroughly homogenized. The mixture is then cooled to about 43–45° C. and packed at 45° C.

Example III

Suntan Cream SPF 30 Utilizing Pre-Prepared Emulsifier

| | Component | Weight % | Class of Compound |
|---|---|---|---|
| Phase A: (mix and dissolve at 85° C.) | Cetyl Phosphate-Borax Adduct Example I, above | 3.5 | Emulsifier |
| | Glyceryl Monostearate, Neutral (Cerasyn SD-ISP) | 4.0 | Thickener |
| | Cetyl Alcohol | 2.0 | Thickener |
| | Marrix ® 2,2,2 Dibehenyl Fumarate Bernel Chemical Co., Inc. | 2.0 | Thickener |
| | Elefac I-205 (Octyl dodecyl Neopentanoate) Bernel Chemical Co., Inc. | 10.0 | Emollient |
| | Octyl Methoxy Cinnamate | 7.5 | Sunscreen |
| | Octyl Salicylate | 5.0 | Sunscreen |
| | Oxybenzone | 5.0 | Sunscreen |
| | Dow Corning Silicone 200–350 cs | 0.5 | Anti-Foamer |
| | Ganen V-220 (PVP-eicosamine-ISP) | 3.0 | Waterproofing polymer |
| Phase B: (Dissolve At 85° C.) | Water, deionized | 56.5 | |
| Phase C | Germaben II (ISP) | 1.0 | Preservative |
| | | 100.0% total | |

The procedure used was as follows:

Phase A and B are mixed well at a temperature of 80–85° C., Phase C is then added to the well mixed A and B mixture and the complete mixture is mixed further until thoroughly homogenized. The mixture is then cooled to about 43–45° C. and packed at 45° C.

Noted here is that the emulsifier, cetyl phosphate borate, prepared in Example I, above, is added to the oil phase, but can also be added to the water phase prior to mixing to produce the final emulsion composition.

Example IV

Water-in-Oil Cream

Using Cetyl Phosphate Borax In Situ as an Auxiliary Emulsifier

The same procedure which was followed for Example III was essentially also followed here, with minor variation.

| | | Weight % |
|---|---|---|
| phase A: (mix at 85–90° C.) | "BSA"(1) | 2.30 |
| | Di Behenyl Fumarate (2) | 8.00 |
| | Di-C$_{12-15}$ Alkyl Fumarate (3) | 10.00 |
| | Di-2-Ethyl Hexyl Fumarate (4) (Octyl Dodecyl NeoPentanoate) | 28.20 |
| | ELEFAC I-205 (5) | 15.00 |

-continued

| | | Weight % |
|---|---|---|
| | Cetyl Phosphate (6) | 0.50 |
| | Propyl Paraben | 0.10 |
| phase B: (mix at 85–90° C.) | Water, deionized | 33.30 |
| | Borax N.F. | 1.35 |
| phase C: | Fumed SiO$_2$ (cabosil) | 1.25 |
| | | 100.0% total |

(1) Mulls ® 2218 (Bernel Chemical Co., Englewood, New Jersey);
(2) commercial as Marrix ® 222 (Bernel);
(3) Marrix ® SF (Bernel);
(4) Bernel ® Ester 284 (Bernel);
(5) Bernel
(6) Amphisol A (Roche)

(1) Mulls ® 2218 (Bernel Chemical Co., Englewood, N.J.)

(2) commercial as Marrix® 222 (Bernel);

(3) Marrix® SF (Bernel);
(4) Bernel® 286 (Bernel);
(5) Bernel
(6) Amphisol A (Roche)

Procedure

Add B to A at 85° C. and mix without aeration. Continue mixing while slowly adding phase C. Mix and cool to 50° C. Package.

Example V

In-Situ Shampoo

|  |  | Weight % |
| --- | --- | --- |
| phase A: (45° C.) | PPG-2-laureth-20-phosphate (1) | 4.0–5.0% |
|  | Fragrance | 1.0% |
| phase B: (mix at 45° C.) | Water, deionized | 91.5–93.0% |
|  | Borax N.F. | 2.0–2.5% |
|  |  | 100.0% total |

(1) $C_{16}$—(PO)$_2$—(EO)$_{20}$H$_2$PO$_3$ (1) $C_{16}$—(PO)$_2$—(EO)$_{20}$H$_2$PO$_3$
PO=Propylene Oxide
EO=Ethylene Oxide Procedure Add phase B to A at 45° C. and mix without aeration. Continue mixing until homogeneous/clear. Cool to 40° C. Package.

Example VI

Solubilized Perfume Solution

|  |  | Weight % |
| --- | --- | --- |
| phase A: (45° C.) | PPG-2-laureth-20-phosphate (1) | 5.0–30.0% |
|  | Foam Stabilizers (2) | 0.1–10.0% |
|  | Thickeners (3) | 0.1–10.0% |
|  | Fragrance | Q.S. |
|  | Preservative | Q.S. |
| phase B: (mix at 85–90° C.) | Water, deionized | Q.S to 100% |
|  | Borax N.F. | 2.5–15.0% |
|  |  | 100.0% total |

(1) $C_{16}$—(PO)$_2$—(EO)$_{20}$H$_2$PO$_3$
(2) e.g. diethanolamine lauramide, coco betaine (oleyl betaine), cocoyl sulfobetaine, among others
(3) e.g. hydroxyethyl cellulose, other cellulose thickeners, sodium stearate, among others.
PO=Propylene Oxide
EO=Ethylene Oxide Procedure Mix phase B at 80° C. Add phase B to A at 80° C. and mix without aeration. Continue mixing until homogeneous/clear. Cool to 50° C. Package.

It is to be understood by those skilled in the art that the foregoing description and examples are illustrative of practicing the present invention, but are in no way limiting. Variations of the detail presented herein may be made without departing from the spirit and scope of the present invention as defined by the following claims.

What is claimed is:

1. A composition comprising: an oil phase and a water phase, said oil phase comprising about 10% to about 90% by weight of said composition and said water phase comprising about 10% to about 90% by weight of said composition, said oil phase comprising about 70% to about 99.75% by weight of an oil and about 0.25% to about 30% by weight of a phosphoric acid ester compound according to the structure:

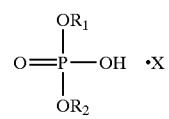

where $R_1$ and $R_2$ are H or a linear, cyclic or branch chained saturated or unsaturated $C_8$–$C_{40}$ hydrocarbon group, a —(R$^3$—O)$_m$—R$^4$ group, a —R$^5$—O—(R$^3$—O)$_m$—R$^4$ group or a

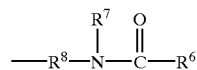

group,
where $R^3$ is a $C_2$–$C_6$ alkylene group or a mixture of ethylene and propylene groups, $R^4$ is H or a linear, cyclic or branch chained saturated or unsaturated $C_8$–$C_{40}$ group, a

group or a

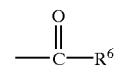

group, $R^5$ is a $C_2$–$C_{18}$ alkylene group, $R^6$ is a linear, cyclic or branch chained saturated or unsaturated $C_8$–$C_{40}$ hydrocarbon group and m is an integer from 0 to 150, $R^7$ is H or a linear, cyclic or branch-chained saturated or unsaturated $C_1$–$C_{22}$ hydrocarbon group or a $C_1$–$C_{22}$ alcohol group and $R^8$ is a $C_1$–$C_{22}$ linear, cyclic or branched chain saturated or unsaturated hydrocarbon group, with the proviso that when $R_1$ is H, $R_2$ cannot also be H; and X is $Na_2B_4O_7$, said composition being free from diethanolamine cetyl phosphate.

2. The composition according to claim 1, wherein $R_1$ is H and $R_2$ is a —(R$^3$—O)$_m$—R$^4$ group.

3. The composition according to claim 2 wherein $R^3$ is an ethylene group, a propylene group or a mixture of ethylene and propylene groups, m is 2 to 20 and $R^4$ is a $C_{16}$ linear or branch chained hydrocarbon group.

4. The composition according to claim 3 wherein $R^3$ is a mixture of ethylene and propylene groups, m is 4 and $R^4$ is a branch chained hydrocarbon group.

5. An emulsion composition comprising:
   1) about 0.5% to about 15% by weight of the reaction product of a phosphoric acid ester compound of the formula:

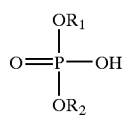

where $R_1$ and $R_2$ are H or a linear, cyclic or branch chained saturated or unsaturated $C_3$–$C_{40}$ hydrocarbon group, a —$(R^3$—$O)_m$—$R^4$ group, a —$R^5$—$(R^8$—$O)_m$—$R^4$ group or a

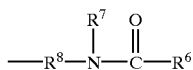

group,
where $R^3$ is a $C_2$–$C_6$ alkylene group or a mixture of ethylene and propylene groups, $R^4$ is H or a linear, cyclic or branch chained saturated or unsaturated $C_8$–$C_{40}$ group, a

group or a

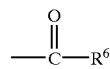

group, $R^5$ is a $C_2$–$C_{18}$ alkylene group, $R^6$ is a linear, cyclic or branch chained saturated or unsaturated $C_8$–$C_{40}$ hydrocarbon group and m is an integer from 0 to 150, $R^7$ is H or a linear, cyclic or branch-chained saturated or unsaturated $C_1$–$C_{22}$ hydrocarbon group or a $C_1$–$C_{22}$ alcohol group and $R^8$ is a $C_1$–$C_{22}$ linear, cylic or branched chain saturated or unsaturated hydrocarbon group, with the proviso that when $R_1$ is H, $R_2$ cannot also be H; and an amount of an active boron salt neutralizing agent effective to neutralize said phosphoric acid ester compound;

2) about 15% to about 89.5% by weight of an oil;
3) optionally, from 0.1% to about 20% by weight of a secondary emulsifier; and
4) about 10% to about 75% water, said composition being free from diethanolamine cetyl phosphate.

6. The composition according to claim 5 wherein said $R_1$ is a $C_{12}$–$C_{22}$ hydrocarbon group, $R_2$ is H and said neutralizing agent is selected from the group consisting of sodium tetraborate decahydrate, sodium tetraborate tetrahydrate and mixtures thereof.

7. The composition according to claim 5 wherein said neutralizing agent is sodium tetraborate decahydrate.

8. The composition according to claim 5 wherein $R_1$ is H and $R_2$ is a —$(R^3$—$O)_m$—$R^4$ group.

9. The composition according to claim 8 wherein $R^3$ is an ethylene group, a propylene group or a mixture of ethylene and propylene groups, m is 2 to 20 and $R^4$ is a $C_{16}$ linear or branch chained hydrocarbon group.

10. The composition according to claim 9 wherein $R^3$ is a mixture of ethylene and propylene groups, m is 4 and $R^4$ is a branch chained hydrocarbon group.

11. A composition comprsing: an emulsion, said emulsion being formed by mixing an oil phase and a water phase, said oil phase comprising about 10% to about 90% by weight of said composition and said water phase comprising about 10% to about 90% by weight of said composition, said oil phase comprising at least about 70% to about 99.75% by weight of an oil; and about 0.25% to about 30% by weight of a phosphoric acid ester compound of the formula:

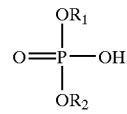

where $R_1$ and $R_2$ are H or a linear, cyclic or branch chained saturated or unsaturated $C_8$–$C_{40}$ hydrocarbon group, a —$(R^3$—$O)_m$—$R^4$ group, a —$R^5$—$O$—$(R^3$—$O)_m$—$R^4$ group or a

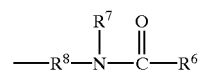

group,
where $R^3$ is a $C_2$–$C_6$ alkylene group, preferably an ethylene group, a propylene group or a mixture of ethylene and propylene groups, $R^4$ is H or a linear, cyclic or branch chained saturated or unsaturated $C_8$–$C_{40}$ group, a

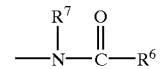

group or a

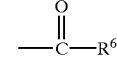

group, $R^5$ is a $C_2$–$C_{18}$ alkylene group, $R^6$ is a linear, cyclic or branch chained saturated or unsaturated $C_8$–$C_{40}$ hydrocarbon group and m is an integer from 0 to 150, $R^7$ is H or a linear, cyclic or branch-chained saturated or unsaturated $C_1$–$C_{22}$ hydrocarbon group or a $C_1$–$C_{22}$ alcohol group and $R^8$ is a $C_1$–$C_{22}$ linear, cylic or branched chain saturated or unsaturated hydrocarbon group, with the proviso that when $R_1$ is H, $R_2$ cannot also be H; and an amount of an active boron salt neutralizing compound effective to produce an emulsion when said oil phase and said water phase are mixed, said composition being free from diethanolamine cetyl phosphate.

12. The composition according to claim 11 wherein said neutralizing compound is selected from group consisting of sodium tetraborate decahydrate, sodium tetraborate tetrahydrate, and mixtures thereof.

13. The composition according to claim 11 wherein $R_1$ is H and $R_2$ is a —$(R^3$—$O)_m$—$R^4$ group.

14. The composition according to claim 13 wherein $R^3$ is an ethylene group, a propylene group or mixture of ethylene and propylene groups, m is 2 to 20 and $R^4$ is a $C_{16}$ linear or branch chained hydrocarbon group.

15. The composition according to claim 14 wherein $R^3$ is a mixture of ethylene and propylene groups, m is 4 and $R^4$ is a branch chained hydrocarbon group.

* * * * *